(12) United States Patent
Sjöholm et al.

(10) Patent No.: US 6,642,016 B1
(45) Date of Patent: Nov. 4, 2003

(54) BIOSENSOR AND ITS USE TO INDICATE THE STATUS OF A PRODUCT

(75) Inventors: Johan Sjöholm, Lund (SE); Per-Olof Erlandsson, Södra Sandby (SE)

(73) Assignee: Bioett AB, Lund (SE)

( * ) Notice: Subject to any disclaimer, the term of this patent is extended or adjusted under 35 U.S.C. 154(b) by 7 days.

(21) Appl. No.: 10/089,181

(22) PCT Filed: Oct. 5, 2000

(86) PCT No.: PCT/SE00/01930

§ 371 (c)(1),
(2), (4) Date: Mar. 27, 2002

(87) PCT Pub. No.: WO01/25472

PCT Pub. Date: Apr. 12, 2001

(30) Foreign Application Priority Data

Oct. 5, 1999 (SE) ................................. 9903617

(51) Int. Cl.⁷ ............................. C12Q 1/48; C12Q 1/34; C12Q 1/58; C12M 1/00
(52) U.S. Cl. ............................. 435/15; 435/18; 435/12; 435/283.1; 435/287.1; 435/289.1
(58) Field of Search ............................. 435/15, 18, 12, 435/283.1, 287.1, 289.1

(56) References Cited

U.S. PATENT DOCUMENTS

| | | |
|---|---|---|
| 2,671,028 A | 3/1954 | Clark |
| 3,977,945 A | 8/1976 | Törnmarck |
| 5,182,212 A | 1/1993 | Jalinski |
| 5,384,028 A * | 1/1995 | Ito .............................. 204/403 |

FOREIGN PATENT DOCUMENTS

| | | |
|---|---|---|
| JP | 3150458 A | 6/1991 |
| JP | 5018931 A | 1/1993 |
| WO | 92/05415 A1 | 4/1992 |
| WO | 93/16938 A1 | 9/1993 |

OTHER PUBLICATIONS

STN International, File MEDLINE, Medline accession No. 78004173, Blixt et al.: "An enzymatic time temperature device for monitoring the handling of perishable commodities"; Developments in biological standardization, (Oct. 1976) 36 237–41.

* cited by examiner

Primary Examiner—Louise N. Leary
(74) Attorney, Agent, or Firm—Burns, Doane, Swecker & Mathis, L.L.P.

(57) ABSTRACT

A biosensor comprises a unit, comprising a substrate and an enzyme, which when brought into contact with the substrate is adapted to affect the substrate so that its conductivity changes as a function of time and temperature, and an electric circuit. The unit is included as a component in said electric circuit and the electric circuit is activable by applying an electric field and/or a magnetic field over the same to generate a measurable signal which is dependent on the total resistance of the circuit. The invention also relates to the use of a biosensor, a label with such a biosensor and a method of indicating the status of a product with such a biosensor.

20 Claims, 2 Drawing Sheets

BIOSENSOR AND ITS USE TO INDICATE THE STATUS OF A PRODUCT

TECHNICAL FIELD

The present invention generally relates to a biosensor. More specifically, the invention relates to a biosensor for indicating the status of a product. The invention also relates to a method of using said biosensor and a label comprising such a biosensor as well as a method of indicating the status of a product by means of the biosensor.

Said status of the product can relate to its durability or indicate to what extent the product has been cooked or heated.

BACKGROUND OF THE INVENTION

In many cases, the status of a product is to a great extent a function of time and temperature.

The status may, for instance, relate to the durability of a product, such as a food or medicinal product. The product continuously changes its status such that the remaining durability continuously decreases. Normally, the product has longer durability if it is kept cool or cold. However, it is not possible to check the durability of a product only by observing the container, in which the product is packaged. Therefore such a product container is often provided with a so-called "best before date". Normally, this "best before date" presupposes that the product is kept at a certain temperature, and if this temperature is exceeded the "best before date" is naturally deceptive. To avoid the selling of products whose durability has expired, a "best before date" is indicated, which expires with a certain margin before the expiration of the durability of the product. This means that still durable products often have to be rejected.

The status can also indicate to what extent, for instance, a food product has been cooked or heated. The product normally gets more and more cooked with increasing time and temperature. Food products can, for instance, be cooked by putting the product and its container in a microwave oven. In that case, it is not possible to check whether the food product is ready-cooked only by looking at the container, but the product is cooked by being heated for a prescribed period of time at a given effect.

Therefore, to be able to determine the status of a product in a more exact manner, different types of labels have been developed, which can be applied to product containers and which monitor the time and the temperature to which the product has been exposed and which thus indicate the status of the product stored in the container.

A first type of such labels, so-called RF tags, comprises an electric circuit with a microprocessor. The microprocessor is adapted to continuously detect and register time and temperature. By determining the status development of the product in advance as a function of time and temperature, such a label can be made to indicate the present status of the product. However, the disadvantage of such labels is that microprocessors of said type are comparatively expensive, resulting in a relatively high manufacturing cost of the labels. As a matter of fact, it is not realistic from an economic point of view to apply such labels to product containers in general, since the cost per label is too high in relation to the price of the product in each container.

A second type of labels comprises a substrate, which is adapted to provide an optically readable change, such as a change of colour, after a certain time and temperature. The optical change can be adapted to coincide with the expiration of the durability of a product. When cooking a food product, for instance when cooking food or drink in a microwave oven, such a label applied to the container can be adapted to provide an optically readable change when the product is prepared. The advantage of these labels or indicators is that they can be manufactured relatively cheap. On the other hand, the disadvantage is that the labels must be read manually. If the labels are applied, for instance, to cartons of milk, each carton of milk and the applied label must be inspected to determine the status of each of the cartons. When cooking food, a change is obtained when the food product is prepared. Thus, the label must be observed continuously to make it possible to interrupt the cooking when the food product is ready. Consequently, this type of label is rather complicated to use.

The above-described second type of labels can be designed as so-called biosensors, where an enzyme causes the desired colour change of the substrate. By using enzymes, the biosensor can be adjusted to the product whose status is to be indicated by the biosensor. Thus, it will be possible to ensure that the colour change takes place at the desired point of time while taking into account the temperature changes to which the product and the biosensor applied thereto have been exposed. However, the problem of optical reading of the result remains to be solved.

SUMMARY OF THE INVENTION

One object of the present invention is to provide an improved biosensor, which is relatively cheap to manufacture and which can be used to indicate the status of a product. The biosensor should also allow simple and rational indication of said status.

Another object of the present invention is to provide a method of using such a biosensor, a label comprising such a biosensor as well as a method of indicating the status of a product by means of such a biosensor.

To achieve the first object, a biosensor is provided in accordance with claim 1. Preferred embodiments are stated in claims 2–6.

To achieve the additional objects, a method of using said biosensor according to claim 7, a label according to claim 8 and a method according to claim 9 are stated. A preferred embodiment of the method is stated in claim 10.

More specifically, according to the present invention a biosensor is defined for indicating the status of a product, said biosensor being characterized by a unit comprising a substrate and an enzyme, which when brought into contact with the substrate is adapted to affect the substrate so that its conductivity changes as a function of time and temperature, and an electric circuit, said unit being included as a component in said electric circuit and said electric circuit being activable by applying an electric field and/or a magnetic field over the same to generate a measurable signal, which is dependent on the total resistance of the circuit.

In this way, a biosensor is provided which can be manufactured at a relatively low cost and which is very suitable for indicating the status of a product. The enzyme is suitably adapted to affect the conductivity of the substrate according to the function, according to which the status of the product is affected under the influence of time and temperature. The signal which is generated when activating the electric circuit is dependent on the total resistance of the circuit. The electric conductibility of the substrate, i.e. its conductivity which is the inverse of the specific resistance of the substrate, affects the total resistance of the circuit. Thus, the signal generated when activating the electric circuit will be dependent on the total resistance of the circuit, which in turn is dependent on the conductivity of the substrate. The signal thus also indicates indirectly, besides the present conductivity of the substrate, the present status of a product which has been exposed to the same time and temperature conditions as the biosensor. When the status development of the product under the influence of time and temperature is known, it can also be possible to make a prognosis for the future status development of the product by assuming future temperature conditions. Finally, the biosensor allows simple and rational indication of said status. The activation of the electric circuit and the reading of the generated signal can be automatized. As a result, it is not necessary to read the respective biosensors manually, whereby it is possible, for instance, to determine the status of a large number of products in an efficient manner.

The electric circuit is activated by applying an electric field and/or a magnetic field over the same. The signal which is generated when activating the circuit is preferably a measurable current induced in the circuit. The circuit is in its turn preferably a so-called oscillation circuit. Thus, a biosensor is provided, whose oscillation circuit is activable by applying, for instance, a magnetic field over the same to generate a measurable current, which is dependent on the total resistance of the circuit and which thus varies as a function of the time and temperature to which the unit of the biosensor has been exposed. As a result, indirect reading of the signal generated by the circuit is possible by reading the actual magnetic field, which is dependent on the current induced in the circuit. The current itself is dependent on the total resistance of the circuit, which resistance in turn is dependent on the present conductivity of the substrate.

According to a preferred embodiment of the inventive biosensor, the enzyme is adapted to affect the substrate so that its conductivity increases as a function of time and temperature.

The enzyme which is included in the unit of the biosensor is preferably selected from one of the following enzyme classes: Transferases, Hydrolases and Lyases. The enzyme which is currently most preferred is Urease, which is an enzyme of the enzyme class Hydrolases.

The substrate which is included in the unit of the biosensor advantageously comprises Urea. According to the present invention, use is also stated of a biosensor as defined above for indicating the status of a product, which exhibits a status development which is affected as a predetermined function of time and temperature, the enzyme being adapted to affect the conductivity of the substrate according to the same function of time and temperature, which product and which biosensor are synchronized concerning said function, the unit of the biosensor being activated by bringing the enzyme into contact with the substrate when applying the biosensor to the product, whereby the present status of the product is indicatable by applying an electric field and/or a magnetic field over the electric circuit, which, as a result, generates a signal that is dependent on the total resistance of the circuit and thus also indicates the conductivity of the substrate.

According to the invention, a label is also defined for application to a product container, said label comprising a biosensor as stated above.

Finally, according to the invention a method is defined of indicating the status of a product, such as a food or medicinal product, located in a container, comprising the steps of (i) determining the status of the product as a function of time and temperature, (ii) adapting the enzyme of a biosensor as stated above to affect the conductivity of the substrate according to the same function of time and temperature, (iii) arranging the biosensor on said container, (iv) activating the unit of the biosensor by bringing the enzyme into contact with the substrate when placing the product in the container, (v) applying an electric field and/or a magnetic field over the electric circuit when the status of the product is to be checked, (vi) measuring the signal which is in this context generated by the electric circuit of the biosensor and which is dependent on the present conductivity of the substrate, and (vii) determining on the basis of said signal the present status of the product.

According to a preferred embodiment, the method comprises the step of storing in a memory unit the measured signal together with data identifying the container on which the biosensor is arranged. This allows a quality assurance, by means of which it is possible to check afterwards to what time and temperature conditions a product has been exposed at a certain point in the handling chain.

The present invention will be described below for the purpose of exemplification with reference to the accompanying drawings.

DESCRIPTION OF EMBODIMENTS

Figure 1:
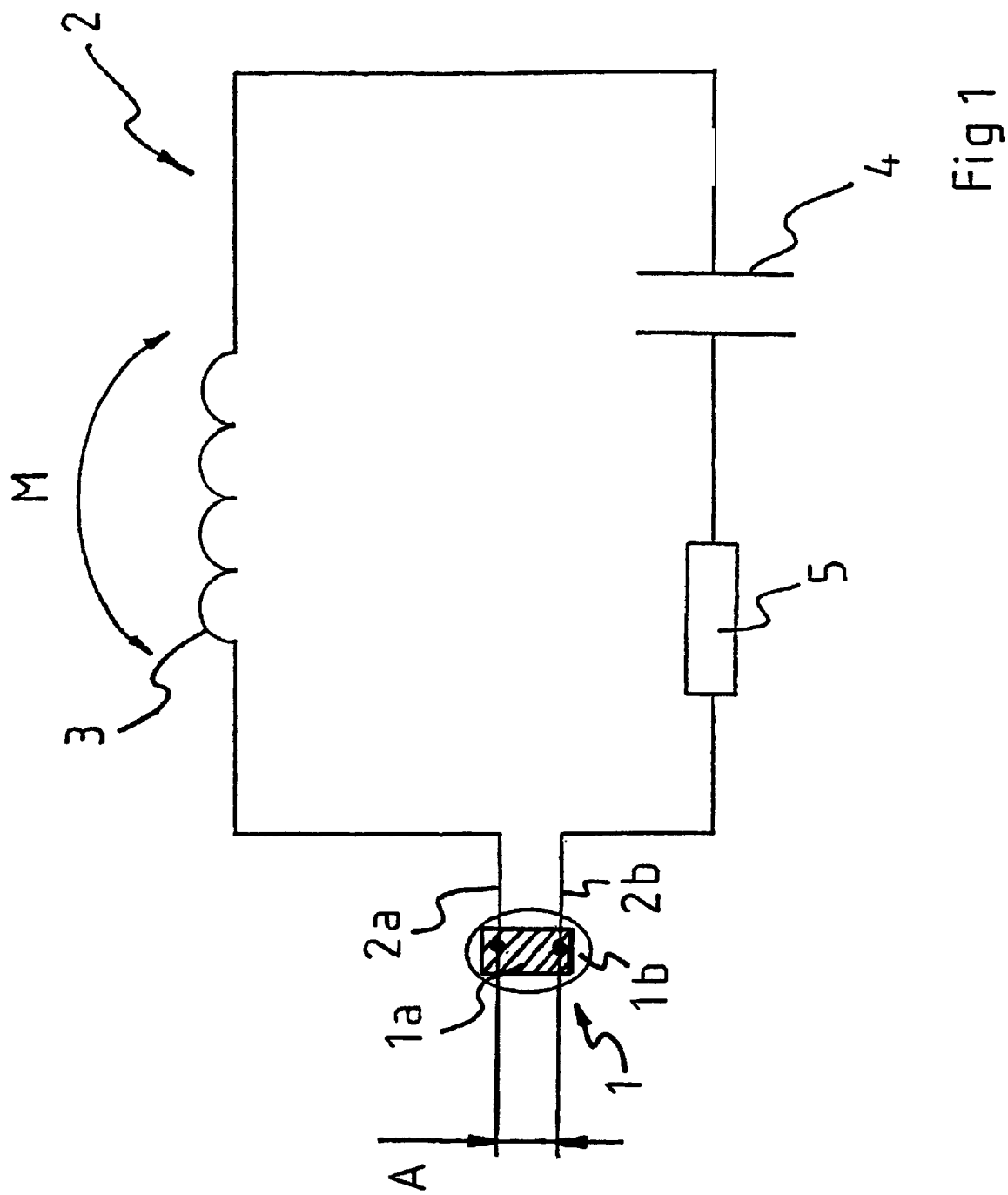
FIG. 1 schematically shows a biosensor according to a preferred embodiment of the present invention.

Reference is now made to FIG. 1, which schematically shows a biosensor according to a preferred embodiment of the present invention. The biosensor comprises a unit 1, including an enzyme 1a and a substrate 1b as well as an electric circuit 2, which is affected by said unit 1 and which is adapted to generate a signal when activated. Due to the fact that the unit 1 affects the electric circuit 2, the unit 1 also affects the signal which is generated when activating the circuit 2.

A basic understanding of the present invention is that certain enzymes can be made to affect the associated substrate so that its conductivity changes. Conductivity is a measure of the electric conductibility of the substrate. Another measure of said electric conductibility is the specific resistance of the substrate, which resistance is the inverse of the conductivity.

Enzymes are proteins which catalyse chemical reactions in living organisms. More specifically, enzymes are composed of amino acids linked to each other in a long chain. This chain folds and forms an intricate three-dimensional structure, which constitutes the basis of the properties of an enzyme. Enzymes have very specific reactions and in a mixture of millions of different but similar substances they can select the right substance. By means of additives, enzymes can also be stabilised so that they can be exposed to high temperatures.

The rate of the reaction catalyzed by the enzyme is dependent on time and temperature.

There are a number of different enzymes, but those relevant to the present invention are thus the ones that cause a change in the conductivity of the substrate. Enzymes that catalyse a reaction, in which as many ions as possible form, are particularly preferred. The reason for this is that the relative change in the conductivity is thus maximized. Enzymes having this property can be found in the following enzyme classes: Transferases, Hydrolases and Lyases.

Hydrolases is the class of enzymes which is currently most preferred and, among the enzymes of this class, the enzyme Urease has been found to be particularly preferred.

Urease catalyses a hydrolyse of Urea as follows:

Urea+water→carbon dioxide+ammonia $H_2NCONH_2 + H_2O + 2H^+ \rightarrow 2NH_4^+ + CO_2$ (reaction catalysed by Urease)

$CO_2 + H_2O \rightarrow HCO_3^- + H^+$ (spontaneous reaction)

A large number of micro-organisms and advanced plants include Urease. Urease is extracted for commercial use from beanstalks. The enzyme has a very high specificity to urea. The enzyme has a molar weight of 480,000 g/mole and has a nickel atom as prosthetic group (is involved in the catalysis).

Urea is a colourless crystalline substance which has a melting point of 132.7° C. and which is also known under the name of carbamide. Urea is present in urine of mammals and is produced in the liver as an end product when decomposing protein. Urea can also be synthesised chemically and is, among other things, used as a source of nitrogen in fertilizers.

Advantageously, the unit 1 of the biosensor shown in FIG. 1 comprises an enzyme 1a in the form of Urease as well as a substrate 1b which comprises Urea. To activate the unit 1 of the biosensor, the enzyme 1a is brought into contact with the substrate 1b, whereby the enzyme Urease catalyses a hydrolyse of Urea as stated above, the conductivity of the substrate 1b thus increasing as a function of time and temperature. Once the enzyme 1a has been brought into contact with the substrate 1b, the conductivity of the latter will vary as a function of time and temperature, which means that the electric conductibility of the substrate 1b will change.

The substrate 1b can also comprise a buffer solution to compensate for pH changes in the substrate 1b. By this means, extreme pH values which may inactivate the enzyme 1a are avoided.

As appears from FIG. 1, the unit 1 forms a component in the electric circuit 2. Furthermore, the electric circuit 2 is a so-called oscillation circuit 2, which is activated by applying an electric and/or magnetic field M over the same. From now on, the description will be directed towards the activation of the circuit by applying a magnetic field over the same. This is not, however, intended to limit the scope of the present invention, and it will be understood that the circuit is activated by supplying energy, which the circuit uses to generate a signal, whose amplitude and duration are dependent on the total resistance of the circuit.

Said oscillation circuit 2 comprises a coil 3, a capacitor 4 and a resistor 5, which are connected in series in a closed circuit. The unit 1 is connected in series with the other components 3, 4, 5. To activate the circuit 2, a magnetic field M is applied over the coil 3 to induce a current in the circuit 2.

More specifically, the current that is induced when applying a magnetic field M over the oscillation circuit 2 will be dependent on the total resistance of the circuit 2. When applying the magnetic field M over the coil 3, a frequency is also generated in the circuit 2. The amplitude of the frequency is dependent on the current and thus also dependent on the total resistance of the circuit 2. Since the enzyme 1a is adapted to change the conductivity of the substrate 1b (and thus also its specific resistance) as a function of time and temperature, said current will be dependent on the present conductivity of the substrate 1b and consequently vary according to the same function of time and temperature. As a result, it will be possible to determine the time and temperature to which the biosensor has been exposed by applying a magnetic field M over the coil 3 and by detecting the thus induced current. This can also be achieved by detecting the amplitude of the frequency which is generated at the same time.

The easiest way of detecting the signal generated by the circuit 2, such as the current or amplitude of the frequency, is to indirectly measure the magnetic field M applied over the circuit 2. As already mentioned, said enzyme 1a is preferably adapted so that the conductivity of the substrate 1b increases as a function of time and temperature, which means that the specific resistance of the substrate 1b decreases. As a result, in the circuit 2 shown in FIG. 1, the magnetic field M will be more and more affected by the circuit 2 the higher the conductivity of the substrate 1b.

The inventive biosensor is very suitable to use when indicating the status of a product, such as a food or medicinal product. The enzyme 1a of the biosensor is adapted to change the conductivity of the substrate 1b according to the function of time and temperature, according to which the product changes its status. This adjustment can be achieved in many different ways. As shown in FIG. 1, the unit 1 is connected to the electric circuit 2 via two electrodes 2a, 2b. In order to close the circuit 2, the substrate 1b must thus exhibit such electric conductibility that a current can flow between the electrodes 2a, 2b, the current intensity being stronger the higher the conductivity. To adapt the biosensor, the distance between the electrodes 2a, 2b can be modified. Moreover, it is possible to modify the cross-sectional area of the substrate 1b. It goes without saying that it is also possible to modify the concentration of the enzyme 1a as well as the substrate 1b. Finally, various buffer concentrations can also be used.

The conductivity of the substrate 1b can thus be used as an indicator of the status of the product.

Figure 3:
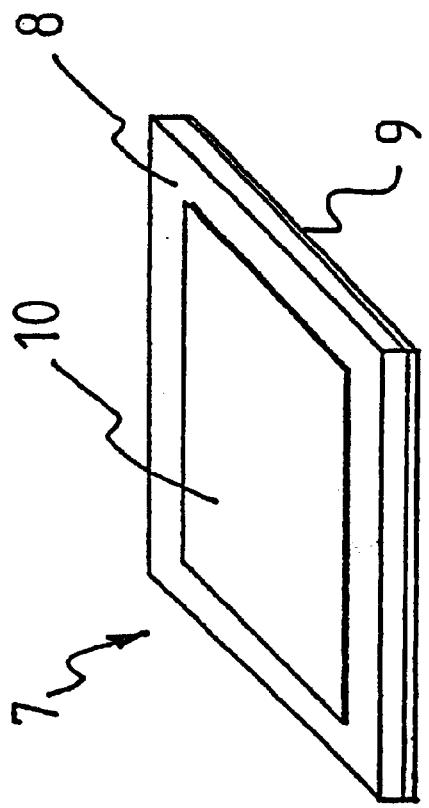
FIG. 3 is a schematic perspective view of a label according to the invention.
Figure 2:
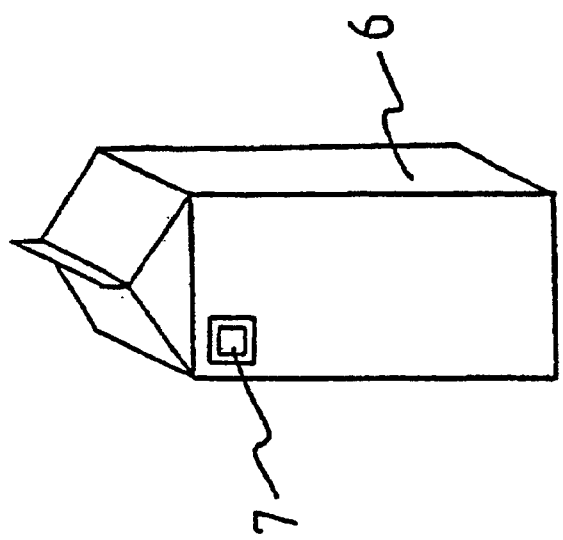
FIG. 2 is a schematic perspective view of a product container, on which an inventive biosensor is arranged.

When used, the inventive biosensor is applied to a container 6, in which the product is located and which is shown in FIG. 2. The biosensor is suitably arranged on a label 7, as schematically shown in FIG. 3. The label 7 comprises, for instance, a carrier 8, to the underside of which an adhesive layer 9 is applied. The biosensor forms a layer 10, which is arranged on the upper side of the carrier 8. In this way, the biosensor can be applied to the container 6 in a simple way.

When reading the biosensor, a magnetic field M is applied, as already mentioned, over the electric circuit 2, and the magnetic field M will be more or less affected as a function of the present value of the conductivity of the substrate 1b. The conductivity of the substrate 1b of the biosensor will develop according to the function, according to which the status of the product develops.

Below, some alternative fields of application of the above-described biosensor will be described.

The biosensor can be used to monitor the time and temperature to which a product has been exposed and thus to indicate indirectly the durability of a product. By ensuring that the expiration of the durability of the product coincides with a certain threshold resistance of the substrate 1b, at which threshold resistance a magnetic field M applied over the biosensor is affected to a predetermined extent, it is easy to indicate the durability of the product.

As already stated, the unit 1 of the biosensor is suitably adapted so that the enzyme 1a affects the substrate 1b so as to increase its conductivity as a function of time and temperature. The unit 1 can thus be considered as a resistor, whose resistance decreases as a function of time and temperature. When the unit 1 of the biosensor has just been activated, the specific resistance of the substrate 1b is at its maximum, and when applying a magnetic field over the circuit 2 the induced current will be at its minimum. The specific resistance of the substrate 1b will then decrease as a function of time and temperature, whereby the induced current will increase when repeatedly applying a magnetic field over the circuit 2.

The signal generated by the circuit 2 will thus vary as a function of time and temperature. Advantageously, this signal is read indirectly by measuring the magnetic field M itself to see how it is affected by the circuit 2. If the resistance of the substrate 1b decreases with time and temperature, the influence of the circuit 2 on the magnetic field M will increase. The relative change of the magnetic field M is thus dependent on the relative current change, which in turn is dependent on the resistance change of the substrate 1b, which resistance change is dependent on the time and temperature to which the biosensor has been exposed.

The biosensor can, for instance, be used together with a food product such as milk. The biosensor is applied to a product container and, when applying a magnetic field M over the same, it emits a signal indicating the present status of the product, for instance, whether the durability of the product has expired.

A medicinal product such as an insulin ampoule may also be involved. The durability of the insulin is very much dependent on the temperature, at which it is stored. Insulin quickly ages even at room temperature. Thus, an insulin user must handle his insulin carefully and make sure that he only injects approved ampoules, i.e. ampoules containing insulin whose durability has not expired. To improve safety when handling such insulin ampoules, an inventive biosensor can be applied to each ampoule. The device, by means of which the insulin in the ampoule is injected in a user, is provided with a means for reading the biosensor and for indicating whether the respective ampoules are approved for use.

The inventive biosensor can also be used when cooking food or drink products, and particularly when cooking in a microwave oven. The biosensor is in this case arranged on the container, in which the product is contained, such as a cardboard box or mug. The unit 1 of the biosensor is, for instance, designed so that a magnetic field M applied over the biosensor is affected by the circuit 2 to a predetermined extent when the biosensor, and thus also the product, has been exposed to a certain temperature for a certain time. In case a microwave oven is used, a device can be mounted in the same for applying the magnetic field M and for detecting said magnetic field M. The microwave oven can be arranged to be turned off when the magnetic field M is sufficiently affected by the circuit 2 of the biosensor as well as to emit a sound signal, which indicates that the product is ready.

It is, of course, essential that the product and the unit 1 of the biosensor be synchronized as concerns the function, according to which the status of the product and the conductivity of the substrate 1 develop.

To provide said synchronization, it is sufficient to determine the basic signal, for instance the basic current in the circuit 2 of the biosensor, when the product is introduced into the container 6. This basic signal can be determined by measuring the present state of the conductivity of the substrate 1b or by activating the circuit 2 of the biosensor for measuring the generated signal. The basic signal corresponds to the original status of the product, i.e. the fresh product.

When the status of the product later is to be indicated, the electric circuit 2 of the biosensor is activated and the generated signal is measured. This signal is compared with said basic signal, whereby a change can be observed. On the basis of this signal change, the conductivity change of the substrate 1b can, for instance, be determined and, with the aid of the information about the influence of the enzyme 1a on the conductivity of the substrate 1b as a function of time and temperature, it is possible to determine the time and temperature to which the biosensor, and thus also the product, has been exposed, which in turn makes it possible to indicate the status of the product.

As a result, the status of the product can be indicated, whenever desired, by activating the electric circuit 2 of the biosensor and by measuring the thus generated signal. Said signal will vary as a function of the conductivity of the substrate and thus also indirectly vary as a function of the status of the product.

Today, enzymes 1a and substrates 1b of the above-mentioned kind can be manufactured at a low cost. It is further possible to manufacture electric circuits, such as the oscillation circuit 2 shown in FIG. 1, at a very low cost. As a consequence, the inventive biosensor can be manufactured at an extremely low cost, and therefore mass production of such biosensors for application to product containers, such as milk cartons or insulin ampoules, is feasible from an economic point of view.

It will be appreciated that biosensors according to the present invention can be used for rational and time-efficient indication of the status of a great number of products. A device can, for instance, be arranged to activate the circuits 2 of the biosensors and to measure and register the thus generated signals. By processing this data, the status of each of the products can then be indicated. Moreover, it may be possible to make prognoses for the remaining durability of the products by assuming the future temperature conditions of the products.

The inventive biosensor also allows the provision of quality assurance when handling, for instance when transporting, sensitive products. After completed transport, the products are conveyed, for instance, to a warehouse via a control station. At this control station, a biosensor is activated in each of the products, the measured signals being stored in a memory unit together with data identifying the associated product. It is also possible to use a biosensor for a group, such as a package, of products, the signal from the biosensor being stored together with data identifying the package in question. It goes without saying that it is also possible to arrange several control stations of this kind at different places in the handling chain of the products. By storing said information, it is possible to go back afterwards and check the time and temperature conditions to which a certain product or a certain group of products have been exposed at various points in said handling chain. In other words, it will be possible to check that the required quality has been achieved when handling the sensitive products.

It will be understood that the present invention is not limited to the shown embodiments. Several modifications and variations are possible within the scope of the invention. The scope of the invention is thus defined only by the appended claims.

What is claimed is:

1. A biosensor for indicating the status of a product, that comprises unit (1), comprising a substrate (1b) and an enzyme (1a) selected from one of the enzyme classes Transferases, Hydrolases and Lyases, which when brought into contact with the substrate (1b) is adapted to affect the substrate (1b) so that conductivity changes as a function of time and temperature, and an electric circuit (2), said unit (1) being included as a component in said electric circuit (2), and said electric circuit (2) being activated by applying an electric field and/or a magnetic field (M) over the product to generate a measurable signal, which is dependent on the total resistance of the circuit (2) and indicates enzyme activity in the product.

2. A biosensor as claimed in claim 1, in which the enzyme (1a) is adapted to affect the substrate (1b) so that its conductivity increases as a function of time and temperature.

3. A biosensor as claimed in claim 1, in which the enzyme (1a) is Urease.

4. A biosensor as claimed in claim 3, in which the substrate (1b) comprises Urea.

5. A biosensor as claimed in claim 1, wherein said signal is a measurable current, which is generated in the circuit (2).

6. A biosensor as claimed in claim 1, wherein said circuit (2) is an oscillation circuit (2).

7. A label (7) for application to a product container (6), comprising a biosensor as claimed in claim 1.

8. A method of indicating the status of a product which is located in a container (6), characterised by the steps of (i) determining the status of the product as a function of time and temperature, (ii) adapting the enzyme (1a) of a biosensor as claimed in claim 1 to affect the conductivity of the substrate (1b) according to the same function of time and temperature, (iii) arranging the biosensor on said container (6), (iv) activating the unit (1) of the biosensor by bringing the enzyme (1a) into contact with the substrate (1b) when placing the product in the container (6), (v) applying an electric field and/or a magnetic field (M) over the electric circuit (2) when the status of the product is to be checked, (vi) measuring the signal which in this context is generated by the electric circuit (2) of the biosensor and which is dependent on the present conductivity of the substrate (1b), and (vii) indicating on the basis of said signal the present status of the product.

9. A method as claimed in claim 8, further comprising the step of storing in a memory unit the measured signal together with data identifying the container (6) on which the biosensor is arranged.

10. A biosensor as claimed in claim 2, in which the enzyme (1a) is Urease.

11. A biosensor as claimed in claim 10, in which the substrate (1b) comprises urea.

12. A biosensor as claimed in claim 2, wherein said signal is a measurable current, which is generated in the circuit (2).

13. A biosensor as claimed in claim 3, wherein said signal is a measurable current, which is generated in the circuit (2).

14. A biosensor as claimed in claim 4, wherein said signal is a measurable current, which is generated in the circuit (2).

15. A biosensor as claimed in claim 2, wherein said circuit (2) is an oscillation circuit (2).

16. A biosensor as claimed in claim 3, wherein said circuit (2) is an oscillation circuit (2).

17. A biosensor as claimed in claim 4, wherein said circuit (2) is an oscillation circuit (2).

18. A biosensor as claimed in claim 5, wherein said circuit (2) is an oscillation circuit (2).

19. A method according to claim 8, wherein the product is a food product.

20. A method of indicating the status of a product which is located in a container (6), comprising the steps of (i) determining the status of the product as a function of time and temperature, (ii) adapting the enzyme (1a) of a biosensor as claimed in claim 2 to affect the conductivity of the substrate (1b) according to the same function of time and temperature, (iii) arranging the biosensor on said container (6), (iv) activating the unit (1) of the biosensor by bringing the enzyme (1a) into contact with the substrate (1b) when placing the product in the container (6), (v) applying an electric field and/or a magnetic field (M) over the electric circuit (2) when the status of the product is to be checked, (vi) measuring the signal which in this context is generated by the electric circuit (2) of the biosensor and which is dependent on the present conductivity of the substrate (1b), and (vii) indicating on the basis of said signal the present status of the product.

* * * * *